(12) United States Patent
Yoneda

(10) Patent No.: US 6,533,429 B2
(45) Date of Patent: Mar. 18, 2003

(54) INSPECTION ILLUMINATOR

(75) Inventor: Kenji Yoneda, Kyoto (JP)

(73) Assignee: CCS Inc., Kyoto (JP)

( * ) Notice: Subject to any disclaimer, the term of this patent is extended or adjusted under 35 U.S.C. 154(b) by 0 days.

(21) Appl. No.: 10/041,608

(22) Filed: Jan. 10, 2002

(65) Prior Publication Data

US 2002/0093809 A1 Jul. 18, 2002

(30) Foreign Application Priority Data

Jan. 12, 2001 (JP) ........................................ 2001-004315

(51) Int. Cl.[7] ................................................. F21V 8/00
(52) U.S. Cl. ........................ 362/31; 362/555; 362/800
(58) Field of Search .......................... 362/31, 800, 249, 362/252, 555

(56) References Cited

U.S. PATENT DOCUMENTS

| | | | | |
|---|---|---|---|---|
| 4,893,223 A | * | 1/1990 | Arnold | 362/800 |
| 5,136,483 A | * | 8/1992 | Schöniger et al. | 362/61 |
| 5,580,163 A | * | 12/1996 | Johnson, II | 362/800 |
| 5,690,417 A | * | 11/1997 | Potdor et al. | 362/800 |
| 5,828,449 A | * | 10/1998 | King et al. | 356/237 |
| 6,053,621 A | * | 4/2000 | Yoneda | 362/31 |
| 6,161,941 A | * | 12/2000 | Tait et al. | 362/800 |
| 6,443,582 B1 | * | 9/2002 | Tarne et al. | 362/31 |

* cited by examiner

*Primary Examiner*—Laura K. Tso
(74) *Attorney, Agent, or Firm*—Armstrong, Westerman & Hattori, LLP.

(57) ABSTRACT

The present invention provides an inspection illuminator capable of reliably detecting defects on the inspection face of articles to be inspected, while making the brightness of light uniform. In this inspection illuminator, a plurality of illuminant rows are provided, in each of which a multiplicity of illuminants 4 are circularly aligned so as to encircle an opening 1K formed approximately in the center; a plurality of annular transparent bodies 6 for dispersing light from the illuminants of the illuminant rows and guiding such light toward the central axis side of the opening 1K are layered in front of such illuminant rows in a state of being optically shielded with shielding means 7; and the light emitting faces 6A of the transparent bodies 6 are formed into an incline plane such that the upper part thereof is closer to the central axis.

11 Claims, 9 Drawing Sheets

(a)

(b)

(a)

(b)

(a)

(b)

INSPECTION ILLUMINATOR

BACKGROUND OF THE INVENTION

1. Field of the Invention

The present invention relates to an inspection illuminator used, for example, upon inspecting the external appearance or scratch marks of products, which are inspection articles, by irradiating light thereto in the likes of a factory, as well as upon inspecting the soldering quality of electronic components that are mounted on a substrate.

2. Description of the Related Art

As an example of such inspection illuminator, there is Japanese Laid-Open Patent Application No. H10(1998)-21717 proposed previously by the applicant of this application. This disclosure disposes a transparent body for diffusing light on the front part of the inner peripheral side of a multiplicity of illuminants (light emitting diodes) aligned circularly in a state where the light emitting face is directed toward the inner peripheral side, and light is thereby applied on the inspection article from a circular exit face of the transparent body.

Nevertheless, with the aforementioned illuminator, since the illuminants are aligned in a single row, light can only be emitted in a fixed direction and only to the same place on the inspection article. Thus, depending on the shape or the like of an inspection article having a three-dimensional shape, there is an inconvenience in that defects cannot be discovered on the inspection face of the inspection article with irradiation from the aforementioned fixed direction.

SUMMARY OF THE INVENTION

In view of the foregoing circumstances, an object of the present invention is to overcome such problem by providing an inspection illuminator capable of reliably detecting whether there are defects on the inspection face of inspection articles.

In order to achieve the foregoing object, with the inspection illuminator of the present invention, a plurality of rows of illuminant rows are provided in which a multiplicity of illuminants are circularly aligned so as to encircle an opening formed approximately in the center; a plurality of annular transparent bodies for dispersing light from the illuminants of the illuminant rows and guiding such light toward the central axis side of the opening are layered at the front part of such illuminant rows in a state of being optically shielded with a shielding means; and the light emitting faces of the transparent bodies are formed into an incline plane, such that the upper part thereof is closer to the central axis.

Therefore, light from the respective illuminant rows moves inside the respective transparent bodies, while reflecting and scattering in a complex manner, without entering the other illuminant row sides, and irradiates the inspection article from an upward position from the exit face (inclined plane) of the terminal end of the respective transparent bodies. Further, since it is possible to make the light from the respective illuminant rows in an optically shielded state, light may be applied to an inspection article from a plurality of illuminant rows at differing angles, and it is also possible to reliably inspect the inspection face by differing the light irradiation position against the inspection article. Moreover, the inspection article to which light is applied may be visually observed through an opening, or inspection of the inspection face may be conducted through imaging with an imaging means.

Light from the respective illuminant rows may be shielded in the vertical direction by juxtaposing a plurality of rows of circularly aligned illuminant rows in the vertical direction in a state where the light emitting face of the respective illuminants are directed toward the inner peripheral face side; and disposing the plurality of transparent bodies in front of such plurality of rows of illuminant rows.

By juxtaposing a plurality of rows of illuminant rows in the vertical direction as described above, the number of illuminants of all illuminant rows to be mounted can be made the same, and it is thereby possible to avoid variations in the light volume to be applied from the respective illuminant rows.

Light of the respective illuminant groups divided into groups may be shielded in the horizontal direction by juxtaposing a plurality of rows of circularly aligned illuminant rows in the vertical direction in a state where the light emitting face of the respective illuminants are directed toward the inner peripheral face side; dividing the multiplicity of illuminants into a plurality of groups in the peripheral direction; and disposing a plurality of annular transparent bodies for guiding light from the illuminant groups divided into groups in the horizontal direction in front of the illuminant groups in a state of being optically shielded.

By juxtaposing a plurality of rows of illuminant rows in the vertical direction as described above, the number of illuminants of all illuminant rows to be mounted can be made the same, and it is thereby possible to avoid variations in the light volume to be applied from the respective illuminant rows.

Light from the respective illuminant rows may be shielded in the horizontal direction by juxtaposing a plurality of rows of circularly aligned illuminant rows in the horizontal direction in a state where the light emitting face of the respective illuminants are directed downward; and disposing the plurality of transparent bodies below such plurality of rows of illuminant rows, respectively.

According to the foregoing structure, light to be emitted from the respective illuminant rows may be efficiently emitted from the exit faces of the transparent bodies disposed below the respective illuminant rows. For example, FIG. 1 through FIG. 3(a), (b) illustrate the plurality of rows of circularly aligned illuminant rows in a state where the light emitting faces of the respective illuminants are directed toward the inner peripheral face side and, here, it is clear from the drawings that the area of the exit faces 6A of the transparent bodies 6 in comparison to the area to which the illuminants 4 are disposed is narrow due to the diameter becoming smaller, particularly that the area of the exit faces 6A positioned upward become narrower, as well as that the distance from the illuminant 4 to the exit face 6A becomes longer for those illuminants 4 positioned upward. In such a state, even if the number of the respective illuminant rows is the same, the volume of light capable of arriving at the exit face 6A from the illuminant 4 will decrease relative to the illuminants 4 positioned upward. Contrarily, as depicted in FIG. 11 and FIG. 12, the area of the exit faces 6A of the transparent bodies 6 in comparison to the area to which the illuminants 4 of the respective illuminant rows are disposed can be made approximately the same by juxtaposing a plurality of rows of circularly aligned illuminant rows in the horizontal direction in a state where the light emitting faces of the respective illuminants are directed downward; and disposing the plurality of transparent bodies below such plurality of rows of illuminant rows, respectively. Thus, it is possible to efficiently transmit light with the transparent bodies and to inhibit the reduction of light volume in comparison to those illustrated in FIG. 1 through FIG. 3(a), (b). In addition, there is another advantage in that the reduction rate of the light volume in any illuminant row may be made approximately even.

The assembly procedure of the illuminator can be conducted quickly by mounting a multiplicity of illuminants on a single substrate so as to structure the plurality of rows of the illuminant rows.

The brightness of light may be made approximately equal and it is also possible to irradiate inspection articles from different angles by forming the inclined plane of the transparent bodies in a gentle curvature face.

The brightness of light may be further made approximately equal as a result of alleviating the directivity of light upon immediately refracting and dispersing the light from the illuminants in a complex manner, by filling the gaps produced between the illuminants and the transparent bodies with filling material such as transparent silicone.

The attenuation caused by the absorption of light can be minimized by forming the shielding means of a reflective layer so as to return the light applied to such shielding means back into the transparent bodies.

A specific illuminant row or a specific illuminant group may be turned on to conduct the inspection of an inspection article by structuring the respective illuminants juxtaposed in the vertical direction or the respective illuminant groups divided into groups in the horizontal direction so as to be capable of being individually turned on and turned off.

Synthetic light in which a plurality of colors are synthesized or differing single-color light through sequential switching can be applied to the inspection article for inspection by differing the color of the respective illuminants juxtaposed in the vertical direction or the respective illuminant groups divided into groups in the horizontal direction by rows or by groups.

The irradiation volume of light of the respective illuminant rows to be applied to the inspection articles may be made to be the same or different by providing an adjustment means for adjusting the irradiation of the light volume to be emitted through the transparent bodies from the respective illuminants juxtaposed in the vertical direction.

DESCRIPTION OF THE PREFERRED EMBODIMENTS

Figure 1:
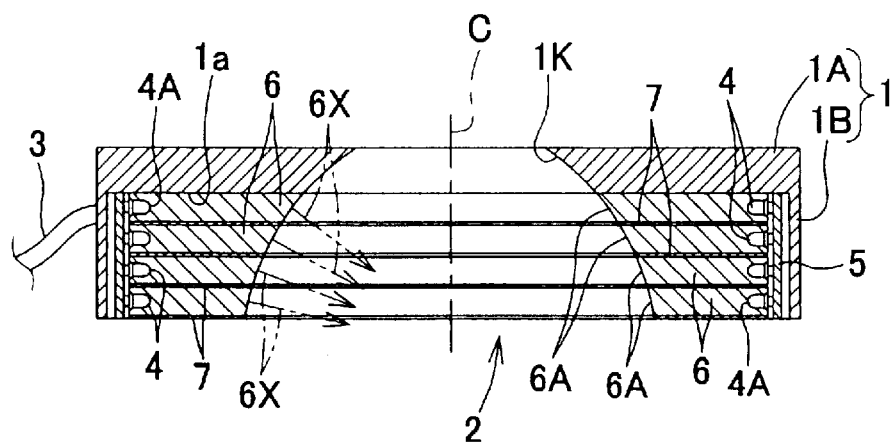
FIG. 1 is a longitudinal cross section of the inspection illuminator.
Figure 2:
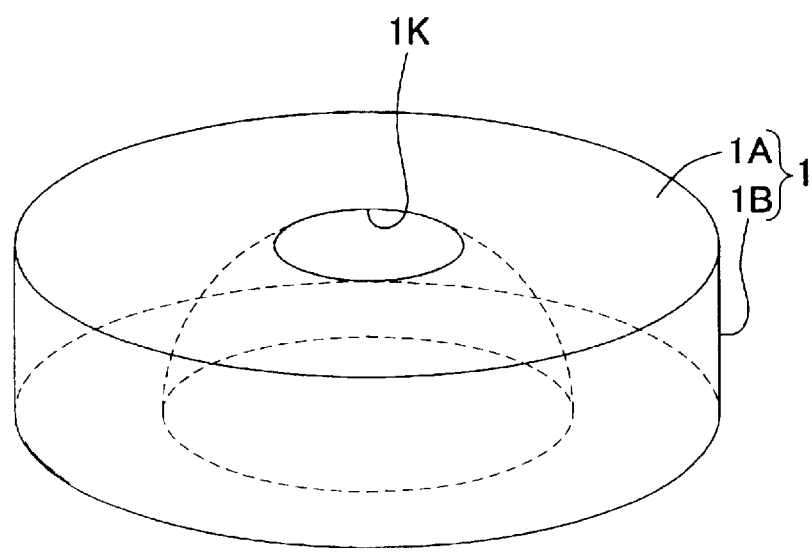
FIG. 2 is a perspective view of the inspection illuminator.

The inspection illuminator of the present invention is illustrated in FIG. 1 through FIG. 3(a), (b). This inspection illuminator has a box shape with the lower part thereof opened, and is structured of a casing 1 having a circular opening 1K in a size enabling visual observation or imaging with the likes of a CCD camera (not shown) as the imaging means at the center of the upper end portion thereof, and a light source 2 provided within this casing 1. Electric power supply to the light source 2 is conducted via a power source cable 3 connected to a substrate 5 described later, and may also be driven with the likes of a secondary battery. This inspection illuminator is mainly used for inspecting the external appearance or scratch marks of products by irradiating light thereto in the likes of a factory and for inspecting the soldering quality of electronic components that are mounted on a substrate, as well as for the purpose of mounting electronic components on a substrate. Images captured with the CCD camera through the opening 1K may be image processed and displayed on a monitor or the like. Although not shown, the inspection illuminator is supported in the state shown in FIG. 1 via other support members and special support members so as to irradiate the inspection article in a downward position.

The casing 1 is positioned such that the lower side thereof is further on the outer peripheral side, and is structured of a circular top plate 1A comprising the opening 1K formed on a gentle curved face (concave face) having a prescribed curvature, and a sidewall 1B suspended from the outer peripheral lower face of this top plate 1A. Nevertheless, the specific structure shall not be limited to the example described above. Although not shown, a through-hole or a helical groove is formed on the sidewall 1B for penetrating the power source cable 3 there through. It is preferable that a reflective layer 7 described later be provided to the lower face 1a of the top plate 1A, but this is not a necessity.

The light source 2 comprises a single substrate 5 for supporting a plurality of rows of illuminant rows (although four rows are illustrated in the drawings, the number of rows may be arbitrary so as long as there are a plurality of rows) in which a multiplicity of light emitting diodes 4, which are illuminants, aligned on the same circumference (circular and annular) having the same center and same radius so as to encircle the opening 1K; a plurality of circular and annular transparent bodies 6 (four in the drawings) for dispersing light from the light emitting diodes 4 of the illuminant rows at the front part of the light emitting face 4A side of such illuminant rows and guiding such light toward the central axis C side of the opening 1K; and a reflective layer (shielding means) 7 in which aluminum or the like is deposited at the lower face of the respective transparent bodies 6 for layering the transparent bodies 6, 6 adjacent in the vertical direction in a state of being optically shielded.

By providing the reflective layer 7 to the upper face of the transparent body 6 positioned in the uppermost vertical part, it is no longer necessary to provide a reflective layer 7 to the lower face of the top plate 1A of the casing 1 as described above. In FIG. 1, although the light emitting diodes 4 of the respective illuminant rows positioned in the vertical direction are disposed in the same positions overlapping in the vertical direction (on the same circumference having the same center and same radius), it would also be possible to reduce the attenuation of light transmitted from the light emitting diodes 4 to the exit faces 6A of the transparent bodies 6 by disposing the light emitting diodes 4 of the illuminant rows positioned higher to a position closer to the exit faces 6A side of the transparent bodies 6 and shortening the distance from the light emitting diodes 4 to the exit faces 6A of the transparent bodies 6.

Figure 4:
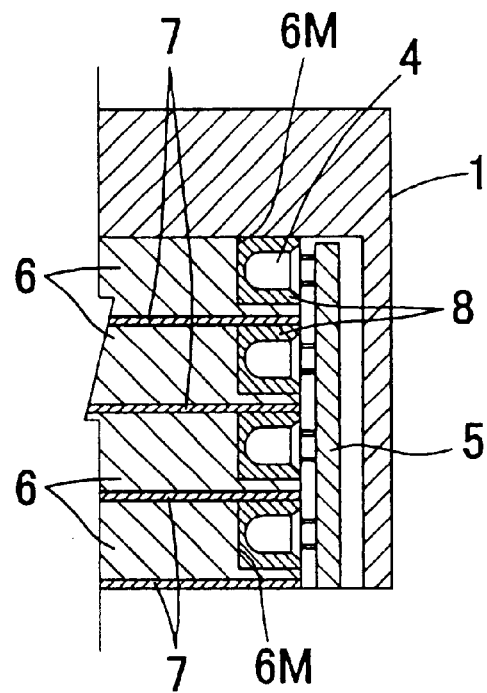
FIG. 4(a) is a cross section of the principle components showing the mounting section of the light emitting diode.
FIG. 4(b) is a cross section showing the shape of the transparent body.
Figure 4:
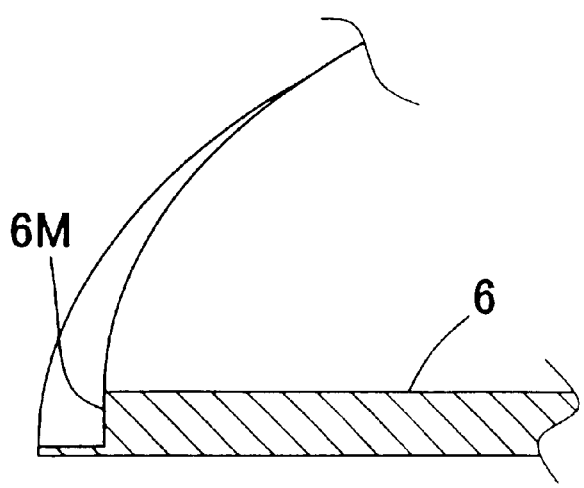

As shown in FIG. 4(a) and FIG. 4(b), an annular groove 6M for incorporating the light emitting diodes 4 is formed on the outer peripheral face of the respective transparent bodies 6. Further, the transparent bodies 6 and 6 are integrated with the likes of adhesives or bolts. The transparent body 6 as used herein refers to a light guiding member (having a plate shape in the drawings) for dispersing and moving the incoming light, and, although it is preferable that the transparent bodies 6 have high transparency since a higher light volume can be transmitted there through, it may have a slightly lower transparency. Further, it is also possible to structure a frosted glass surface by providing minute concavities and convexities on the exit faces 6A of the transparent bodies 6 in order to attain the advantage of obtaining a further even brightness as a result of the light being dispersed upon being emitted from the exit faces 6A. Nevertheless, processing of a frosted glass surface is not a necessity.

As shown in FIG. 1, the exit faces 6A of the plurality of transparent bodies 6 positioned in the upper part are positioned further toward the central axis C side, and are structured in a gentle curvature (concave shape) so as to enable the changing of the irradiation angle against the inspection article. The plurality of transparent bodies 6 in which the exit faces 6A are structured beforehand in a prescribed curvature may be layered and integrated; for example, a plurality of transparent bodies 6 having the same shape may be layered and integrated, and the exit faces 6A may thereafter be processed in the aforementioned shape. Processing the exit faces 6A after layering the plurality of transparent bodies 6 as described above is advantageous in that the precision of the adjacent exit faces 6A in the vertical direction will be improved. Moreover, it is possible to improve the reflectance by employing a reflective layer 7 in which aluminum is deposited thereto. Nevertheless, although the reflectance will decrease somewhat, a reflective layer coated white (or another color) may also be used, or mirror surface processing may be implemented by polishing the lower face of the transparent bodies 6 instead of deposition or coating.

Figure 5:
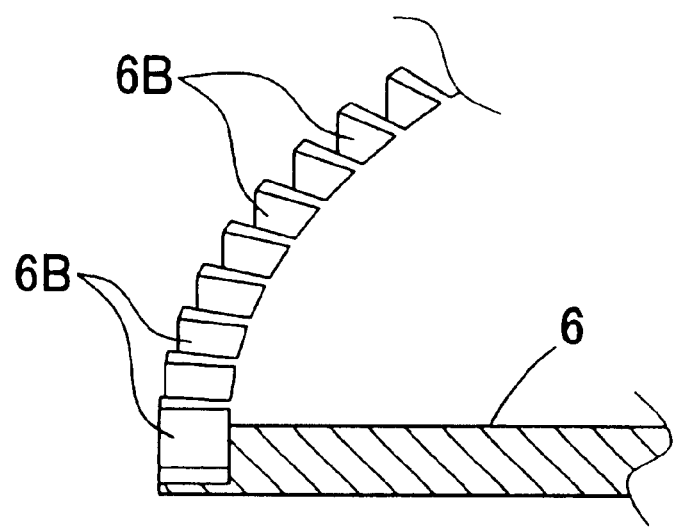
FIG. 5 is a cross section showing another transparent body.

Since the groove 6M creates a helix only in the upper part of the outer periphery of the discoid transparent bodies 6 across the entire circumference as shown in FIG. 4(a) and forms a step portion having an approximate L-shaped cross section, there is an advantage in that the processing precision of the transparent bodies 6 may be made rough in comparison to those having formed therein concave portions 6B for incorporating the individual light emitting diodes 4 in suitable intervals at the upper part of the outer peripheral end of the discoid transparent bodies 6 as shown in FIG. 5. The grooves 6M may be structured in a shape other than those shown in the drawings.

Figure 6:
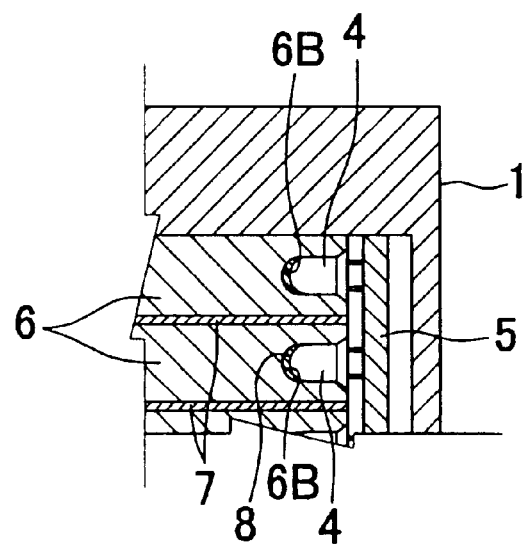
FIG. 6(a) and FIG. 6(b) are cross sections of the principle components showing the mounting section of another light emitting diode.
Figure 6:
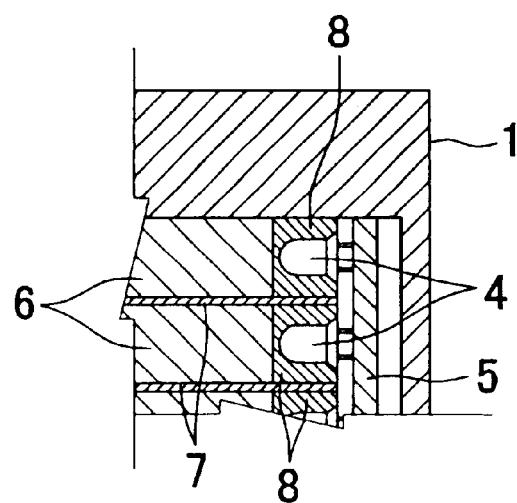

Moreover, the concave portions 6B may be formed at the center of the upper and lower portions of the outer peripheral face of the transparent bodies 6 such that the light emitting diodes 4 can substantially be incorporated therein as shown in FIG. 6(a). Here, the concave portions 6B will require precision. Further, the outer peripheral portion of the transparent bodies 6 may be cut as shown in FIG. 6(b). Reference numeral 8 in FIG. 4(a), FIG. 6(a), (b) is transparent silicone described later.

Figure 7:
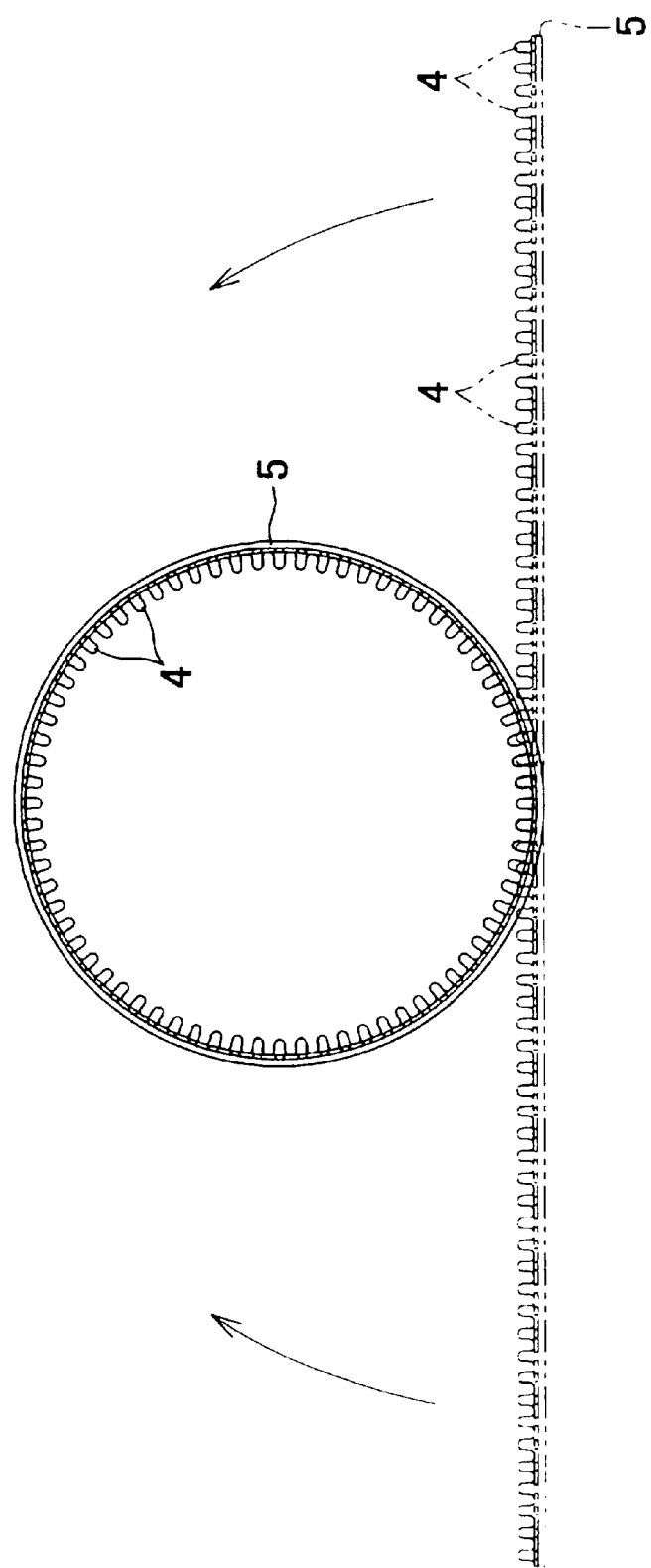
FIG. 7 is an explanatory diagram for making the substrate with a light emitting diode mounted thereon into a circular shape.

The substrate 5 is structured of flexural material and, as shown in FIG. 7, a multiplicity of light emitting diodes 4 are mounted on the substrate 5 zonally formed in a straight line in a state of four parallel rows (c.f. FIG. 1) in a straight line placed in suitable intervals along the entire longitudinal direction thereof. In other words, as shown with the two-point chain line in FIG. 7, regarding the respective light emitting diodes 4, by penetrating and establishing a lead wire perpendicularly against the substrate 5 in which the light emitting faces 4A thereof are of the same posture facing upward and thereafter curving the substrate 5 in the direction of the arrow shown in FIG. 7, the light emitting faces 4A of every light emitting diode 4 will be in a state of facing inward. Here, although not shown, by winding the light emitting faces 4A of every light emitting diode 4, in a state where they are facing inward, on the outer peripheral face of the layered and integrated transparent bodies 6, every light emitting diode 4 of the four upper and lower rows can be incorporated into the grooves 6M of the four upper and lower rows, respectively. By curving the substrate 5 in an annular shape after mounting the light emitting diodes 4 in the same posture against the substrate 5 as described above, there is an advantage in that the mounting procedures of the light emitting diodes 4 can be improved in comparison to the case of mounting the light emitting diodes 4 in a prescribed posture on the substrate 5 formed in an annular shape from the beginning.

Moreover, as shown in FIG. 4(a), by filling the gaps arising between the grooves 6M and the light emitting faces 4A of the light emitting diodes 4 with transparent silicone 8 as the filling material, there is an advantage in that the light from the light emitting diodes 4 can be immediately refracted and dispersed in a complex manner so as to seek the evenness of the brightness upon alleviating the directivity of light. Nevertheless, the filling material may be omitted if sufficient illumination functions can be achieved for certain inspection items. In addition to the transparent silicone 8, various transparent filling materials may be used as the aforementioned filling material.

Upon irradiating light to inspection articles with the illuminator structured as described above, for example, every light emitting diode 4 mounted on the substrate 5 may be turned on (ON) in order to enable irradiation on the inspection article from four different angles (shown with the light axis 6X emitted from the transparent body 6 in FIG. 1) by applying light from four transparent bodies 6 disposed in the vertical direction. Or, drive control may be implemented such that the four rows of illuminant rows are sequentially turned on (ON) one row at a time and, after a prescribed time elapses, turning one row off (OFF) and then turning the next illuminant row on (ON) such that only one illuminant row is sequentially turned on (ON). Further, the illuminant color may be changed for each illuminant or the inside of the respective illuminant rows may be structured of light emitting diodes having different illuminant colors. Moreover, provided may be an adjustment means for adjusting the irradiation of the light volume to be emitted through the transparent bodies 6 from the respective illuminant rows.

Figure 8:
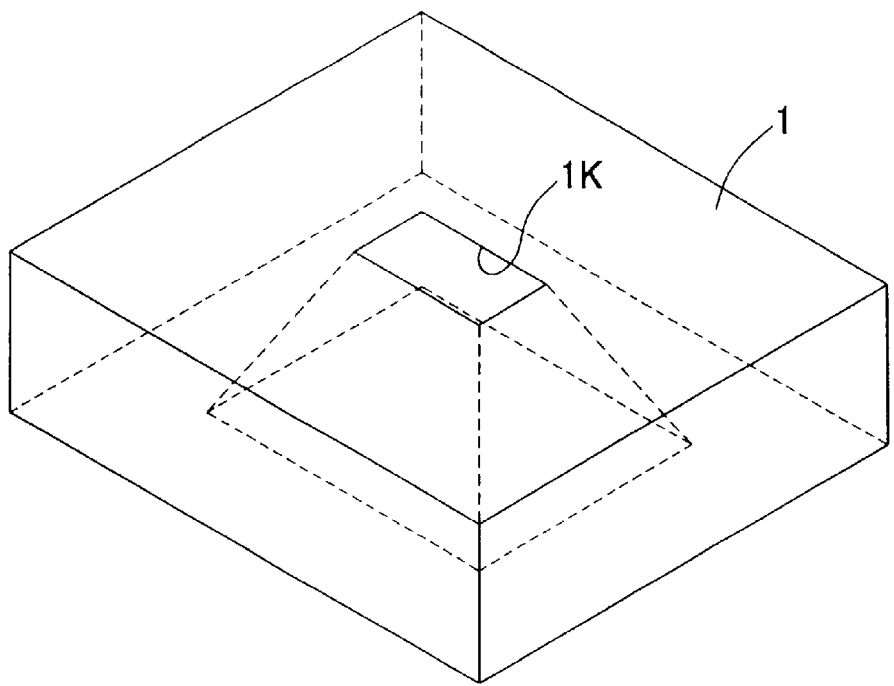
FIG. 8 is a perspective view of another inspection illuminator.
Figure 9:
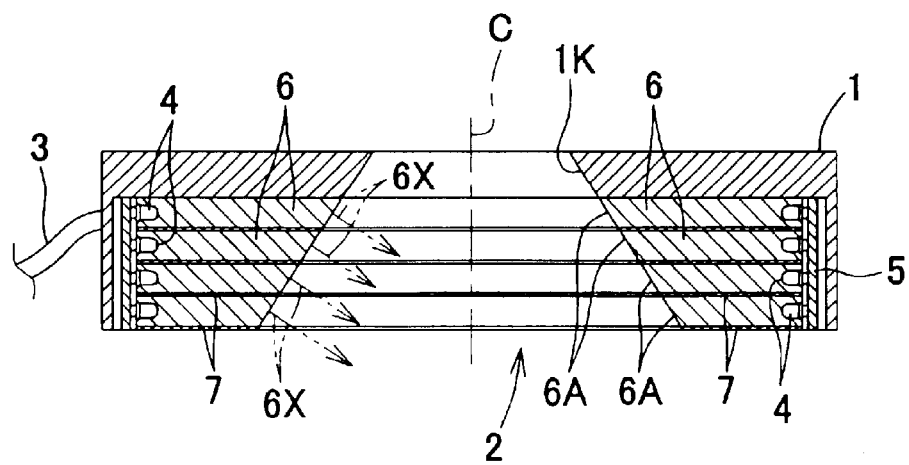
FIG. 9 is a longitudinal cross section of the inspection illuminator illustrated in FIG. 8.

The inspection illuminator may also be structured as illustrated in FIG. 8 and FIG. 9. In other words, a square (or rectangular) casing 1 in a two-dimensional view is used, and the substrate 5, transparent bodies 6 and reflective layers 7 are formed in a square in a two-dimensional view in accordance therewith, and the exit faces 6A of the transparent bodies 6 are formed in a trapezoid as shown in FIG. 9; that is, the exit face 6A of the transparent body 6 positioned toward the upper side is formed on a linear taper face positioned on the central axis C side of the opening 1K, but it may also be a curvature face (concave face) similar to the aforementioned description. By forming the exit faces 6A on this type of linear taper face, the light axis 6X from the respective exit faces 6A becomes parallel, as shown in the two-point chain line of FIG. 9, and inspection of the inspection article may be conducted by changing the irradiation position of the inspection article by switching the illumination drive of the illuminant rows disposed in the vertical direction as described above. Moreover, the illuminant color for each illuminant row may be similarly changed, or the inside of the respective illuminant rows may be structured of light emitting diodes of different illuminant colors. Further, provided may be an adjustment means for adjusting the light volume to be emitted through the transparent bodies 6 from the respective illuminant rows.

Figure 10:
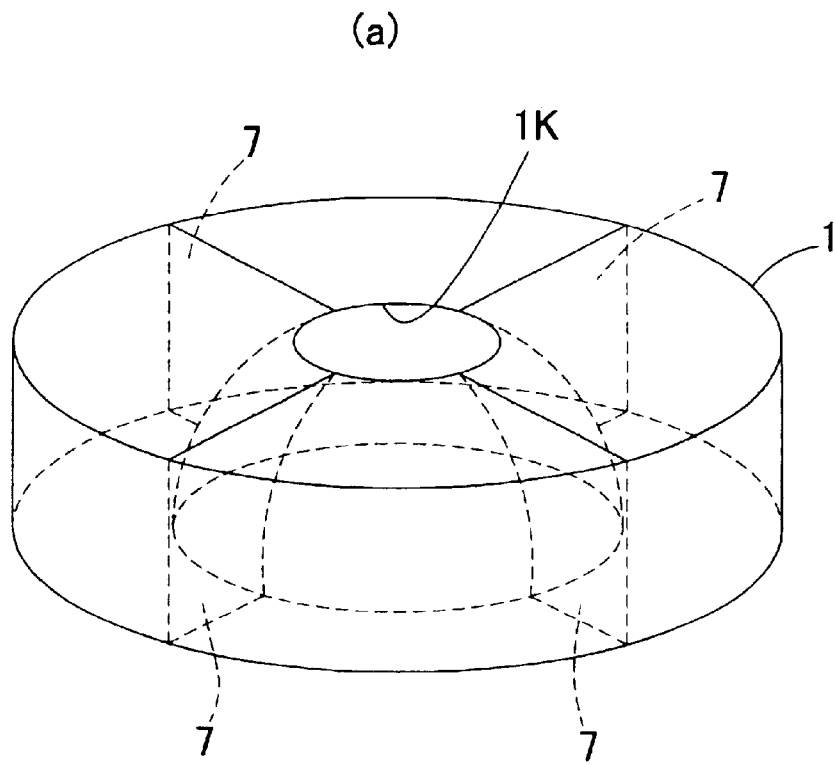
FIG. 10(a) is a perspective view of another inspection illuminator.
FIG. 10(b) is a longitudinal cross section of the inspection illuminator illustrated in FIG. 10(a)
Figure 10:
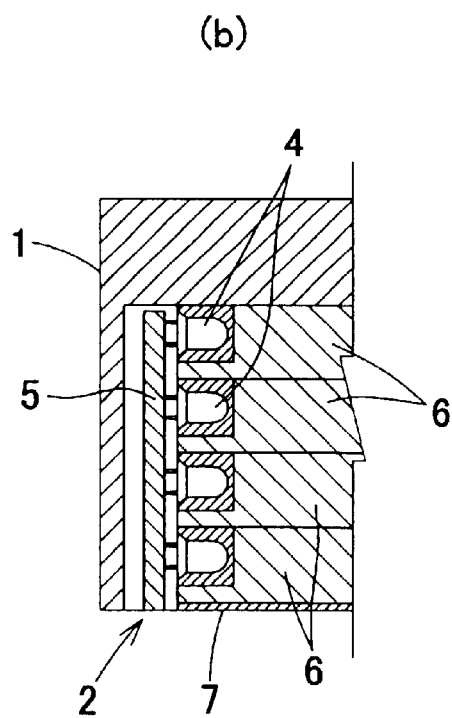

Although the light emitting diodes 4 were divided in the vertical direction in FIG. 1 and FIG. 9, as shown in FIG. 10, they may be structured by being divided into a plurality of groups (although there are four groups in the drawings, the number of groups may be arbitrary so as long as there are a plurality of groups) in the horizontal direction. In other words, the four transparent bodies 6 are formed in an approximate rectangular parallelepiped that is viewed as a fan-shape in a top plan view, a cylindrical transparent body 6 group is structured by combining these four transparent bodies 6, and the light emitting diodes adjacent to each other in the horizontal direction are optically shielded by providing a reflective layer 7 to at least one of the mating faces of the two mating faces of such transparent bodies 6. Further, a reflective layer 7 is also provided to the lower face of the transparent body 6 positioned at the lowermost end. Here, it is possible to conduct inspection of the inspection article by sequentially illuminating only one of the light emitting diode groups among the light emitting diode groups divided horizontally. Moreover, by mutually shielding the respective rows of the four rows of light emitting diode rows layered vertically in FIG. 10(b) with the reflective layer 7 (not shown), the light emitting diode rows may be divided into sixteen in total and, for example, it would be possible to sequentially illuminate an arbitrary row among the light emitting diode rows in f our upper and lower stages structuring an arbitrary light emitting diode group, and to further sequentially illuminate an arbitrary row among the light emitting diode rows in four upper and lower stages structuring the next light emitting diode group after the illumination of one light emitting diode group is completed. By dividing the illuminant sections into sixteen sections, not only is it possible to perform irradiation from four different angles by sequentially illuminating the light emitting diode rows in the vertical direction, it is also possible to perform irradiation from four different locations by sequentially illuminating light emitting diode rows of different locations in the horizontal direction, which is advantageous upon inspecting the inspection articles. Further, although the number of divisions was sixteen in the foregoing example, the division may be set to a number other than sixteen, and more the division, the more advantageous it is upon inspecting the inspection articles. Moreover, the illuminant color for each illuminant row may be similarly changed, or the inside of the respective illuminant rows may be structured of light emitting diodes of different illuminant colors. Further, provided may be an adjustment means for adjusting the light volume to be emitted through the transparent bodies 6 from the respective illuminant rows.

Figure 3:
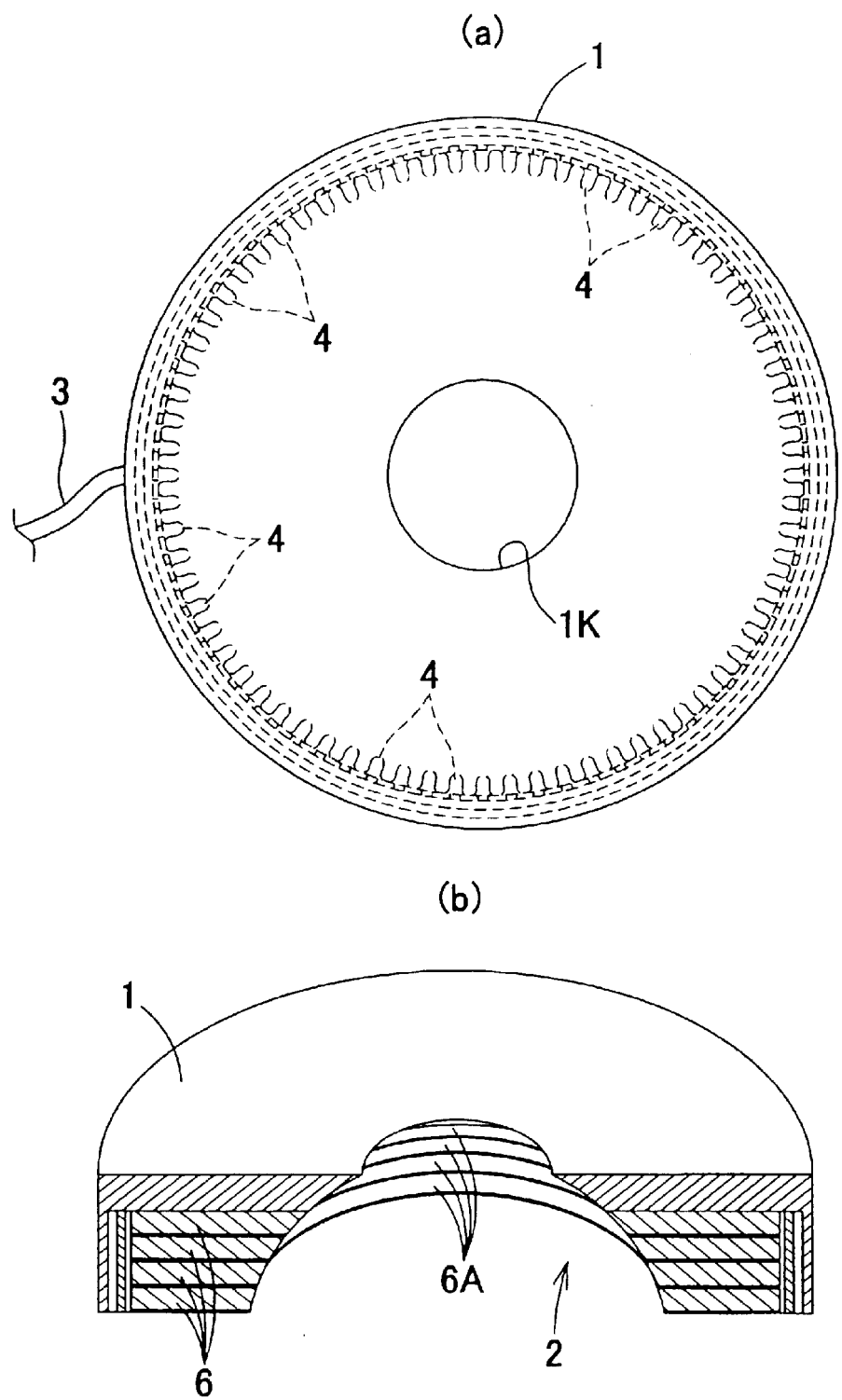
FIG. 3(a) is a plan view of the inspection illuminator.
FIG. 3(b) is a diagram viewed from an upper oblique position upon cutting the inspection illuminator in the longitudinal direction.
Figure 11:
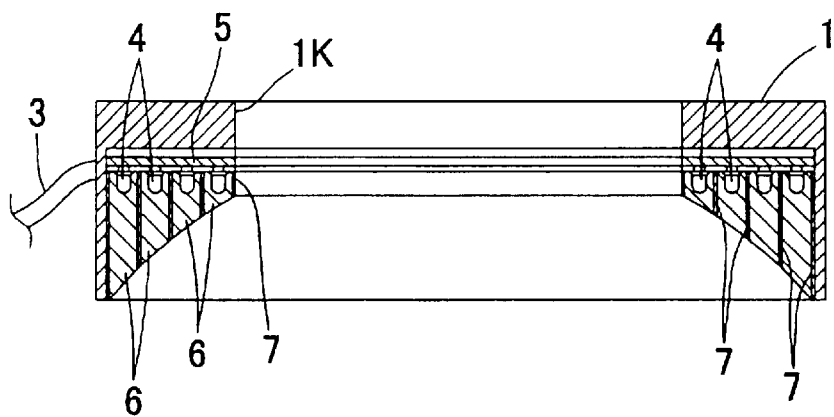
FIG. 11 is a longitudinal cross section of another inspection illuminator.
Figure 12:
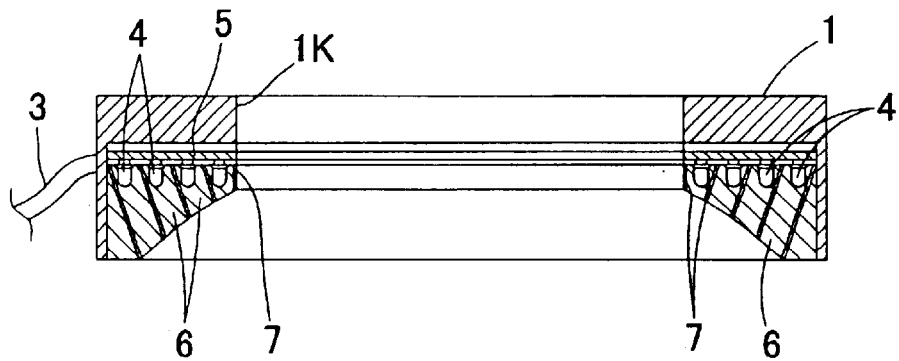
FIG. 12 is a longitudinal cross section of another inspection illuminator.

In addition, the inspection illuminator may be structured as illustrated in FIG. 11 and FIG. 12. In other words, although it is advantageous from the perspective of manufacture by dividing the light emitting diodes 4 in the vertical direction as depicted in FIG. 1 through FIG. 3(a), (b) and FIG. 9, the area of the exit faces 6A, which will be the inner side, will be narrower in comparison to the mounting area of the light emitting diodes 4. Particularly, the exit face 6A positioned upward will be narrower (c.f. FIG. 3(b)), and there is a disadvantage in that the light from the light emitting diodes 4 cannot be efficiently emitted from the exit faces 6A. Nevertheless, as illustrated in FIG. 11 and FIG. 12, it would be possible to juxtapose in a concentric circle a plurality of rows of illuminant rows aligned circularly in a state where the illuminant faces of the respective light emitting diodes 4 are facing downward such that light from any light emitting diode 4 of any illuminant row is efficiently transmitted to the exit faces 6A of the transparent bodies 6. Further, the flexural substrate 5 as shown in FIG. 7 will no longer be necessary by juxtaposing the light emitting diode rows in the horizontal direction as described above, and not only will this lower the cost on substrates, the substrate 5 does not have to be bent, thereby yielding an advantage of improving the precision of the mounting angle of the light emitting diodes 4 on the substrate 5. Moreover, since the diameter becomes smaller toward the inner side, the number of light emitting diodes 4 to be mounted will become smaller for the illuminant rows positioned toward the inner side. Nevertheless, the efficiency will improve since the number of light emitting diodes per unit area of the exit face 6A will be the same. Further, since the transparent bodies 6 are processed obliquely in FIG. 12, this is advantageous for seeking miniaturization of the illuminator in the vertical direction in comparison to the example shown in FIG. 11.

According to the first aspect of this invention, provided is an inspection illuminator capable of reliably detecting scratch marks and defects of inspection articles such as inferior soldering which were conventionally overlooked by irradiating the inspection article, as conventionally, from an upward position from the exit faces of the terminal end of the respective transparent bodies, while also irradiating light to the inspection face of inspection articles from a plurality of illuminant rows at differing angles or differing the light irradiation position against the inspection article.

By structuring the three types of illuminators described in the second aspect through the fourth aspect of this invention, there is an advantage in that the illuminators may be used properly in accordance with the inspection article, and defects in inspection articles can be reliably detected in a broad range.

Moreover, in the case of the fourth aspect of this invention, in comparison to the second aspect and the third aspect of this invention, it is possible to efficiently transmit light with the transparent bodies and to inhibit the reduction of the light volume, as well as to make the reduction rate of the light volume in any illuminant row approximately the same. This is advantageous from the perspective of light transmission efficiency as well as upon being used as an inspection light.

According to the fifth aspect of this invention, the assembly procedure of the illuminator can be conducted quickly by mounting a multiplicity of illuminants on a single substrate so as to structure the plurality of rows of the illuminant rows, thereby yielding an advantage from the perspective of manufacturing costs.

According to the sixth aspect of this invention, the brightness of light may be made approximately equal and it is also possible to irradiate inspection articles from different angles by forming the inclined plane of the transparent bodies in a gentle curvature face, thereby yielding an advantage for light irradiation in determining the soldering quality particularly in fine portions.

According to the seventh aspect of this invention, the brightness of light may be further made approximately equal as a result of alleviating the directivity of light upon immediately refracting and dispersing the light from the illuminants in a complex manner, by filling the gaps produced between the illuminants and the transparent bodies with filling material such as transparent silicone, thereby enabling a further reliable detection.

According to the eighth aspect of this invention, the attenuation caused by the absorption of light can be minimized by forming the shielding means of a reflective layer so as to return the light applied to such shielding means back into the transparent bodies, thereby enabling irradiation of light having a large light volume to the inspection article.

According to the ninth aspect of this invention, a specific illuminant row or a specific illuminant group may be turned on to conduct the inspection of an inspection article by structuring the respective illuminants juxtaposed in the vertical direction or the respective illuminant groups divided into groups in the horizontal direction so as to be capable of being individually turned on and turned off, thereby structuring an illuminator advantageous for certain inspection articles.

According to the tenth aspect of this invention, synthetic light in which a plurality of colors are synthesized or differing single-color light through sequential switching can be applied on the inspection article for inspection by differing the color of the respective illuminants juxtaposed in the vertical direction or the respective illuminant groups divided into groups in the horizontal direction by rows or by groups, thereby structuring an illuminator advantageous for certain inspection articles.

According to the eleventh aspect of this invention, the volume of light of the respective illuminant rows to be applied to the inspection articles may be made to be the same or different by providing an adjustment means for adjusting the light volume to be emitted through the transparent bodies from the respective illuminants juxtaposed in the vertical direction, thereby yielding an advantage providing compatibility with various inspection articles.

What is claimed is:

1. An inspection illuminator, wherein a plurality of illuminant rows are provided in each of which a multiplicity of illuminants are circularly aligned so as to encircle an opening formed approximately in the center; a plurality of annular transparent bodies for dispersing light from the illuminants of said illuminant rows and guiding such light toward the central axis side of said opening are layered at the front part of such illuminant rows in a state of being optically shielded with a shielding means; and the light emitting face of said transparent bodies are formed into an inclined plane, such that the upper part thereof is closer to the central axis.

2. An inspection illuminator according to claim 1, wherein a plurality of rows of circularly aligned illuminants are juxtaposed in the vertical direction in a state where the light emitting face of said respective illuminants are directed toward the inner peripheral face side; and said plurality of transparent bodies are disposed in front of such plurality of rows of illuminants.

3. An inspection illuminator according to claim 1, wherein a plurality of rows of circularly aligned illuminants are juxtaposed in the vertical direction in a state where the light emitting face of said respective illuminants are directed toward the inner peripheral face side; said multiplicity of illuminants are divided into a plurality of groups in the peripheral direction; and a plurality of said transparent bodies for guiding light from the illuminants divided into groups in the horizontal direction are disposed in front of said illuminant groups in a state of being optically shielded.

4. An inspection illuminator according to claim 1, wherein a plurality of rows of circularly aligned illuminants are juxtaposed in the horizontal direction in a state where the light emitting face of said respective illuminants are directed downward; and said plurality of transparent bodies are disposed below the plurality of illuminant rows, respectively.

5. An inspection illuminator according to any one of claims 1 to 4, wherein said multiplicity of illuminants are mounted on a single substrate so as to constitute said plurality of illuminant rows.

6. An inspection illuminator according to any one of claims 1 to 4, wherein the inclined plane of said transparent bodies is formed in a gentle curvature face.

7. An inspection illuminator according to any one of claims 1 to 4, wherein gaps produced between said illuminants and said transparent bodies are filled with a filling material such as transparent silicone or the like.

8. An inspection illuminator according to claim 1, wherein said shielding means is constituted by a reflective layer for returning the light applied to the shielding means back into said transparent bodies.

9. An inspection illuminator according to any one of claims 2 to 4, wherein the illuminant rows juxtaposed in the vertical direction or the illuminant groups divided in the horizontal direction are constructed so as to be capable of being turned on and turned off individually for each row or each group.

10. An inspection illuminator according to any one of claims 2 to 4, wherein the illuminant rows juxtaposed in the vertical direction or the illuminant groups divided in the horizontal direction have different colors respectively.

11. An inspection illuminator according to claim 2 or claim 3, comprising an adjustment means for adjusting the light volume to be emitted through said transparent bodies from the respective illuminant rows juxtaposed in said vertical direction.

* * * * *